United States Patent [19]

Tatum, Jr.

[11] Patent Number: 4,531,915
[45] Date of Patent: Jul. 30, 1985

[54] DENTAL IMPLANT

[76] Inventor: O. Hilt Tatum, Jr., 1 Beach Dr. Southeast, St. Petersburg, Fla. 33701

[21] Appl. No.: 650,573

[22] Filed: Sep. 14, 1984

Related U.S. Application Data

[63] Continuation of Ser. No. 407,942, Aug. 13, 1982, abandoned, which is a continuation-in-part of Ser. No. 303,577, Aug. 14, 1981, abandoned.

[51] Int. Cl.³ .................................................. A61C 8/00
[52] U.S. Cl. .................................... 433/173; 433/176
[58] Field of Search ............... 433/173, 174, 175, 176, 433/201, 220, 221; 3/1.9, 1.91, 1.911, 1.912, 1.913; 128/92 C, 92 CA, 92 BC

[56] References Cited

U.S. PATENT DOCUMENTS

| | | | |
|---|---|---|---|
| 1,479,508 | 1/1924 | Maeulen et al. | 433/221 |
| 2,719,522 | 10/1955 | Hudack | 128/92 CA |
| 2,835,033 | 5/1958 | Airosser | 433/173 |
| 2,835,035 | 5/1958 | Rauscher | 433/175 |
| 3,474,537 | 10/1969 | Christensen | 433/174 |
| 3,497,953 | 3/1970 | Weissman | 433/173 |
| 3,589,011 | 6/1971 | Sneer | 433/174 |
| 3,672,058 | 6/1972 | Nikoghossian | 433/174 |
| 3,683,501 | 8/1972 | Edelman | 433/176 |
| 3,849,887 | 11/1974 | Brainin | 433/173 |
| 3,950,850 | 4/1976 | Driskell et al. | 433/173 |
| 3,952,414 | 4/1976 | Shovers et al. | 433/173 |
| 4,060,896 | 12/1977 | Wahnish | 433/174 |
| 4,109,382 | 8/1978 | Koch | 433/176 |
| 4,177,562 | 12/1979 | Miller et al. | 433/174 |
| 4,217,100 | 8/1980 | Edelman | 433/176 |
| 4,231,120 | 11/1980 | Day | 433/173 |
| 4,234,309 | 11/1980 | Sellers | 433/174 |
| 4,252,525 | 2/1981 | Child | 433/173 |
| 4,253,833 | 3/1981 | Edelman | 433/173 |
| 4,302,188 | 11/1981 | Driskell | 433/173 |
| 4,324,550 | 4/1982 | Reuther et al. | 433/174 |

FOREIGN PATENT DOCUMENTS

| | | | |
|---|---|---|---|
| 2413883 | 9/1975 | Fed. Rep. of Germany | 433/173 |
| 2628929 | 1/1977 | Fed. Rep. of Germany | 433/173 |
| 978502 | 4/1951 | France | 433/173 |
| 1030690 | 6/1953 | France | 433/173 |
| 1305478 | 1/1973 | United Kingdom | 433/173 |

Primary Examiner—John J. Wilson
Attorney, Agent, or Firm—Frijouf, Rust & Pyle

[57] ABSTRACT

A dental implant is disclosed for rigidly anchoring a prosthesis to a jawbone implant site. The first embodiment of the dental implant comprises a center post having a boss connected to the proximal end thereof. A plurality of fins extend radially outward along the center post along the entire longitudinal length thereof. The boss includes a counterbore and a threaded hole for receiving a support cone having a threaded stud extending therefrom. Alternatively, the boss defines a socket for the reception of a correspondingly shaped plug disposed on the support cone. The base has disposed thereon a circumferential sleeve of ceramic material. The second embodiment of the dental implant comprises a major post having a plurality of elongated fins extending radially outward from both sides of the major post. The proximal end of the major post includes a similar counterbore and a threaded hole for receiving the stud of the support cone. One or more minor posts may be connected traversely through the elongated fins to add rigidity thereto. In each embodiment, the support cone is configured to receive a prosthesis. The angle of the support cone with respect to the dental implant may be altered by angling the stud with respect to the support cone. A washer is provided for connection between the support cone and the boss or the proximal end of the major post for varying the rotational position of the tilted support cone with respect to the dental implant.

23 Claims, 16 Drawing Figures

FIG. 9

DENTAL IMPLANT

REFERENCE TO RELATED APPLICATIONS

This application is a continuation of application Ser. No. 407,942, filed Aug. 13, 1982, and now abandoned which is a continuation-in-part of application Ser. No. 303,577, filed Aug. 14, 1981 and now abandoned.

BACKGROUND OF THE INVENTION

1. Field of the Invention

This invention relates to prosthodontic implants for rigidly securing a prosthesis in a natural or a prepared jawbone socket.

2. Description of the Prior Art

Presently there exist many types of dental implants designed to enable a prosthesis such as a crown replacement to be rigidly secured to the jawbone. Probably the most common type of dental implant consists of a threaded pin which is dimensioned to threadably engage the socket of a recently extracted tooth. U.S. Pat. Nos. 3,589,011 and 4,234,309 and German No. 2,255,916 are illustrative examples of such threaded-type implants. The primary disadvantage to the threaded implants in their tendency to loosen within the socket. The implant then has to be removed and replaced by a larger diameter implant. For obvious reasons, these threaded-type implants have not become widely accepted in the art.

U.S. Pat. No. 3,835,033 discloses another type of implant which is designed to be inserted within the socket or alveolar cavity of a recently extracted tooth. More particularly, this type of implant comprises two posts which are inserted into the socket. A plurality of fins and spacers are alternatively slipped onto the posts extending from the socket, with the length of the spacers determining the distance between adjacent fins. The total number of fins and spacers are selected to achieve the desired height of the implant and correspondingly, the amount by which the implant extends from the socket. The implant is left within the socket for a period of time sufficient to enable the bone structure to grow between the adjacent fins. The prosthesis is then connected to the exposed end of the post. A primary disadvantage to this particular implant is the requirement that the implant be assembled piece by piece into the socket of the extracted tooth. This not only increases the difficulty of installing the implant but also increases the likelihood that one of the component pieces will be aspirated by the patient. Moreover, the numerous separate pieces, each of which must be machined to extreme tolerances, increases the overall cost of manufacture of these dental implants. For these reasons, although this type of implant overcomes many of the disadvantages of a screw-type dental implant, it has not been widely accepted in the trade due to its complexity.

U.S. Pat. No. 4,060,896 discloses a threaded-type dental implant wherein a hardenable material is disposed in the jawbone socket prior to the implant being threaded therein. The purpose of the filler material is to assure that the implant will not loosen within the socket of the extracted tooth. It is anticipated that the material will be compressed into the immediately adjacent area of the jawbone as the implant is threaded into the socket. When the material hardens, the implant will be bonded to the bone structure of the jawbone. It should be noted that the filler material must be composed of a hardenable material which will not be rejected by the body.

U.S. Pat. No. 3,672,058 illustrates another threaded-type dental implant which comprises a self-tapping conical screw. The taper of the self-tapping screw is designed such that the implant will threadably engage the socket of the extracted tooth and then threadably engage the portion of the jawbone located immediately below the socket. The socket may be filled with a hardenable resin prior to installing the implant therein. The resin is selected to increase the resistance to rejection of the implant and to avoid deformations of the jawbone.

It should be appreciated that the primary disadvantage to each of the above-described threaded-type implants is their tendency to loosen within the socket after a relatively short period of time. In order to overcome such a tendency, threaded-type implants such as the one disclosed in U.S. Pat. No. 3,474,537 have been developed which are designed to threadably engage through the lower jawbone such that the head of the implant fits against the underside of the jawbone and the terminal end of the implant extends above the jawbone and the gum tissue for providing support to a prosthesis. The head of the implant comprises a flat configuration with one or more holes extending obliquely therethrough. A threaded fastener, such as a screw, is then provided for insertion through the oblique holes to threadably engage the lower portion of the lower jawbone thereby preventing rotation of the implant. Unfortunately, this type of implant can only be utilized when securing a prosthesis to the lower jawbone, and cannot be used for securing a prosthesis to the upper jawbone. Further, a relatively tedious surgical procedure is necessary to properly install the implant.

Therefore it is an object of this invention to provide an apparatus which overcomes the aforementioned inadequacies of the prior art devices and provides an improvement which is a significant contribution of the advancement of the dental implant art.

Another object of this invention is to provide a dental implant which is rigidly secured within the socket or aleveolar of an extracted tooth to provide a suitable foundation for a prosthesis such as a crown.

Another object of this invention is to provide a dental implant which does not threadably engage the socket or alveolar of the extracted tooth, but rather is inserted into the socket and allowed to remain therein for a period of time until the bone structure or spongy medullary of the jawbone grown about the implant thereby rigidly securing the implant in the jawbone.

Another object of this invention is to provide a dental implant having a plurality of fins which extend radially from a central post, the surface area of the fins being substantial to provide adequate support upon vertical loading of the implant.

Another object of this invention is to provide a dental implant having an elongated design with a narrow width for insertion into an artificially created hole in the jawbone.

Another object of this invention is to provide a dental implant which is particularly suitable to be inserted into an artificially created hole in the posterior maxilla to elevate the bony floor of the maxillary sinus thereby creating an equate receptor site in the bone when naturally none existed.

Another object of this invention is to provide a dental implant for insertion into an artificially created hole in the jawbone wherein fins extend radially from a cental post with the outer portions of the fins being interconnected by one or more minor posts which extend parallel to the major post.

Another object and advantage of the present invention is the provision of a boss which is integral with the proximal end of the major post, with the boss having a circumferential sleeve of ceramic material.

The foregoing has outlined some of the more pertinent objects of the invention. These objects should be construed to be merely illustrative of some of the more prominent features and applications of the present invention. Many other beneficial results can be attained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a dental implant designed to be inserted within the socket of a recently extracted tooth or into an artificially created socket in the jawbone. More particularly, the first embodiment of the dental implant comprises a post having a plurality of fins which extend radially therefrom. The size of the fins disposed along the length of the post progressively decreases from the proximal end of the post to the distal end of the post to create a tapered configuration of the dental implant. A boss is integrally formed at the proximal end of the post for threadably receiving a support cone corresponding in shape to a normal tooth preparation which is accomplished prior to crown placement. Alternatively, the boss defines a socket for the reception of a correspondingly shaped plug disposed on the support cone. The boss has a circumferential sleeve of ceramic material. During use, the dental implant is inserted within the socket of a recently extracted tooth. The dental implant is then left in place for a period of time sufficient to allow the bone structure of the jawbone to grow between adjacent fins. A cap screw may be threaded into the boss to prevent matter from entering into and contaminating the threads in the boss. After the dental implant becomes rigidly secured into the bone structure of the jawbone, the cap screw is unthreaded from the boss and a support cone is then threaded into the boss. The support cone includes a shape substantially similar to a normal tooth preparation The prosthesis, such as a crown, is then secured to the support cone by an adhesive or the like.

A second embodiment of the dental implant of the invention operates in a manner similar to the first embodiment, but includes a structure which is substantially different. Specifically, the second embodiment of the dental implant includes a major post having a plurality of fins extending radially therefrom. The fins are integrally formed with the major post and include a substantially long but narrow configuration with the major post being positioned offset from the center of the fins. One or more secondary posts are provided which extend through the outer portions of the fins to add rigidity to the fins. Because of its configuration this second embodiment of the dental implant is designed to be inserted into an artificially created hole in the jawbone. However, it is pointed out that this second embodiment of the dental implant is particularly suitable to be utilized in the posterior maxilla to be used for the elevation of the bony floor of the maxillary sinus thereby creating an equate receptor site in the bone when none naturally existed.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 19 is a top view of FIG. 8 illustrating the configuration of the fins which extend radially from the major post.

Similar reference characters refer to similar parts throughout the several views of the drawings.

DETAILED DESCRIPTION

Figure 1:
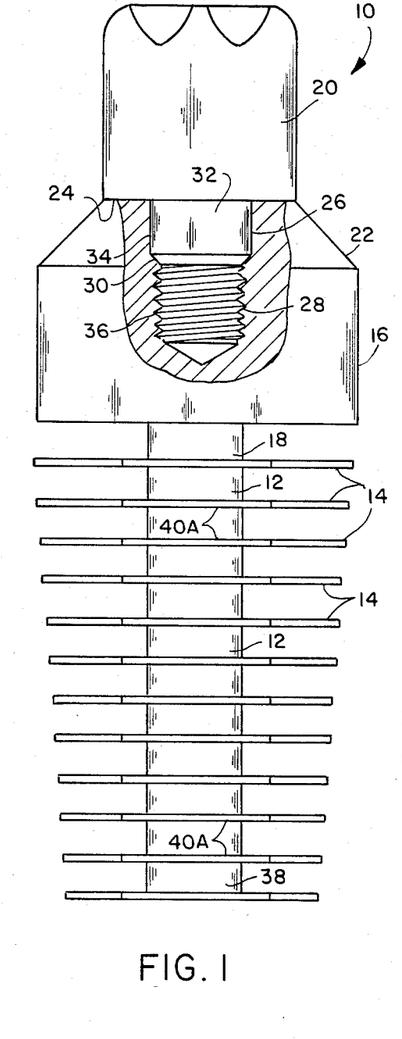
FIG. 1 is a side view of the first embodiment of the dental implant of the invention partially broken away for showing the interior threads of the boss to which the support cone is connected.

FIG. 1 is a side view of the first embodiment of the dental implant 10 of the invention. The first embodiment of the dental implant 10 comprises a central post 12 having a plurality of fins 14 extending radially therefrom. Preferably the fins 14 are equally spaced along the longitudinal length of the post 12 and are integrally formed with the post 12. A boss 16 is integrally formed at the proximal end 18 of the post 12. The boss 16 threadably receives a support cone 20 to which the prosthesis, such as a crown, is connected.

More particularly, the upper corner 22 of boss 16 is chamfered such that the diameter of the supper surface 24 of boss 16 is substantially equal to the diameter of the support cone 20. A counterbore 26 is axially disposed within the upper surface 24 of boss 16. A threaded hole 28 extends concentrically from the bottom of the counterbore 26 into a substantial length of the boss 16. Preferably the diameter of counterbore 26 is appreciably greater than the diameter of the threaded hole 28 to provide a chamfered seat 30 at the junction thereof. The support cone 20 comprises a stud 32 extending axially from the bottom thereof. The stud 32 comprises a shank portion 34 and a threaded portion 36. Preferably the length of the shank portion 34 is substantially equal to the depth of the counterbore 26 such that the end of the shank portion 34 seats against the chamfered seat 30 of the boss 16 when the support cone 20 is threaded into the threaded hole 28. Further, the exposed end of the support cone 20 preferably comprises a shape corresponding to a normal tooth preparation which is accomplished prior to crown placement.

Figure 2:
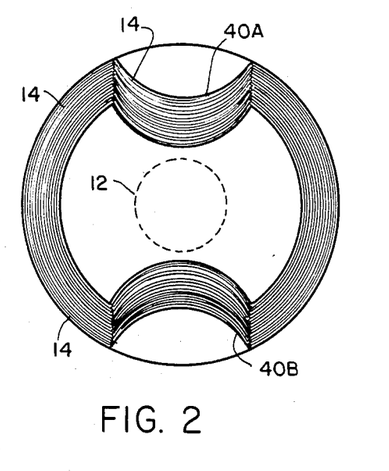
FIG. 2 is a bottom view of FIG. 1 showing the keyways disposed in opposing sides of each of the fins.

As noted earlier, the fins 14 are integrally formed with the post 12 and extend radially outward therefrom. As shown in FIGS. 1 and 2, each fin 14 comprises a substantially flat circular configuration. The sizes of each of the fins 14 progressively decrease from the proximal end 18 of post 12 to the distal end 38 of the post 12 such that the overall diameter of the post 12 and fins 14 combination tapers downwardly from the proximal end 18 to the distal end 38 of post 12. Preferably the taper of the dental implant 10 is designed to correspond to the taper of the socket from which the tooth was extracted. As shown in FIG. 2, a keyway 40A and 40B is cut within opposing sides of each of the fins 14. Each keyway 40A and 40B is semi-circularly shaped and is disposed in a substantial portion of the fin 14. It is noted that the first fin 14 located at the proximal end 18 of post 12 need not include the keyways 40A and 40B.

Figures 1A, 3C, 11:
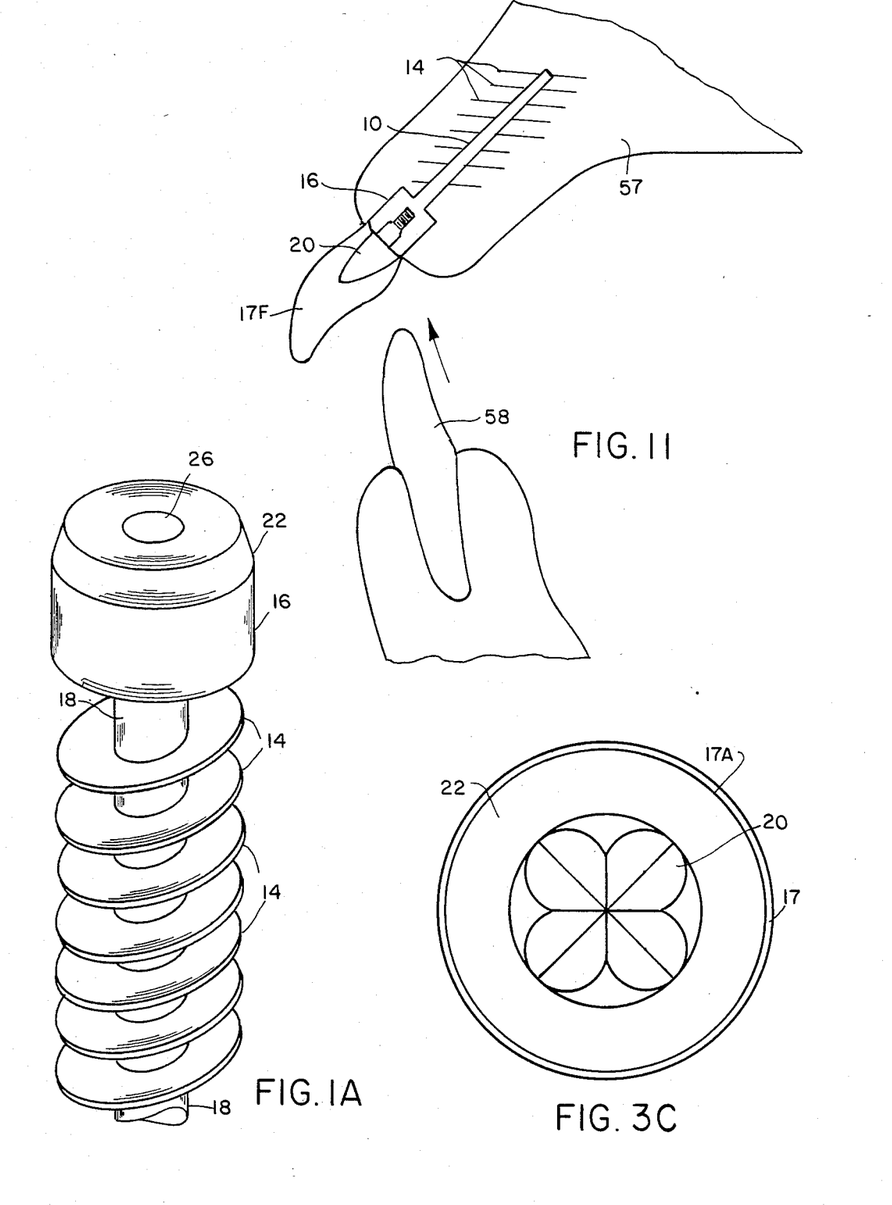
FIG. 1A is a partial perspective view of the dental implant showing the plurality of fins extending obliquely to the center post.
FIG. 3C is a top plan view of FIG. 3A.
FIG. 11 is a side view of the dental implant shown in FIG. 1A when sited in the anterior maxilla.

FIG. 1A is a partial perspective view of the dental implant 10 showing the plurality of fins 14 extending obliquely to the central post 12. Preferably, fins 14 include a circular cross-sectional configuration angularly disposed about the central post 12. It should be understood that the keyways 40A and 40B may be disposed within the fins 14 of the dental implant 10 without departing from the spirit and scope of this invention.

Figure 3:
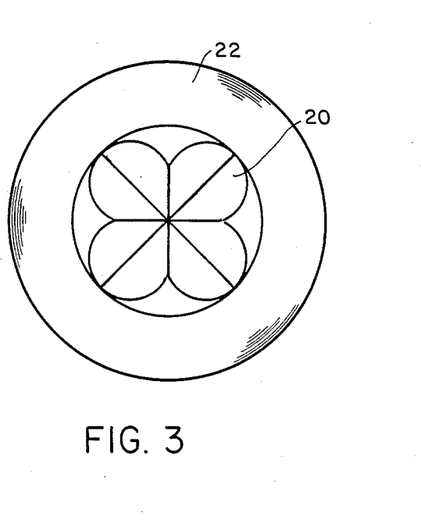
FIG. 3 is a top view of FIG. 1.
Figure 3A:
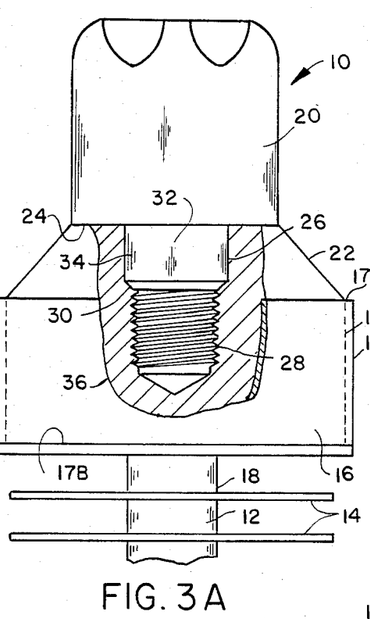
FIG. 3A is a side view of the first embodiment of the present invention partially broken away to show the interior threads of the boss and to show the circumferential sleeve.
Figure 3B:
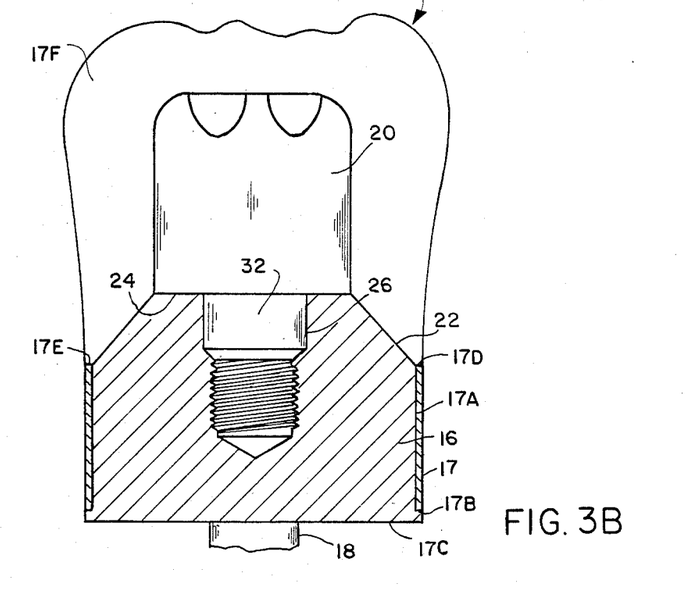
FIG. 3B is a side view similar to FIG. 3A showing a crown located adjacent the circumferential sleeve.

FIGS. 3A, 3B and 3C illustrate a circumferential sleeve 17 surrounding the sidewall of the boss 16. The sleeve 17 lies adjacent to the sidewall 17A of boss 16. The lower edge of sleeve 17 abuts against a circumferential ledge 17B disposed near the bottom surface 17C of boss 16. The upper edge 17D of the sleeve 17 is disposed adjacent the lower edge of the chamfered upper corner 22 of the boss 16 where the upper corner 22 joins the sidewall 17A of the boss.

The upper edge 17D abuts against the outer lower circumferential edge 17E of a crown 17F. The circumferential sleeve 17 may be of a ceramic material such as aluminum oxide. The sleeve 17 may be fastened to the sidewall 17A of the boss 16 by mechanical means such as by suitable cement or may be deposited thereon by sputtering or any other coating process.

As shown in FIG. 3B, the lower outer circumferential edge 17B of the crown 17F abuts against the upper edge 17D of the sleeve 17 thus providing a non-metallic outer surface for contact with the adjacent gingival mucosa membrane.

Figure 3D:
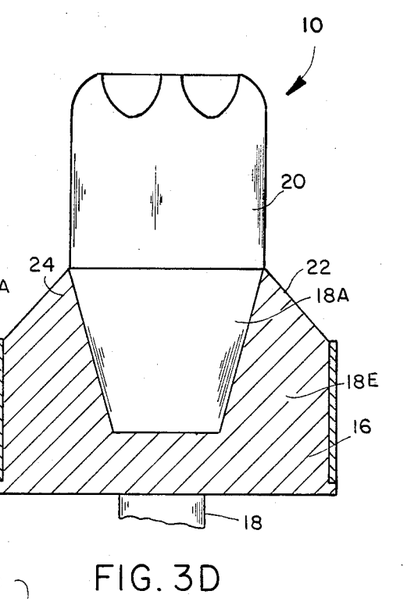
FIG. 3D is a side view of an alternative means for securing the support cone to the boss partially broken away to show the plug and socket means.

FIG. 3D shows an alternative means for connecting the support cone 20 to the boss 16 and includes a tapered plug 18A which is received by a correspondingly tapered socket 18B defined by the boss 16. The plug 18A is of conical configuration such that it form an interference fit with the socket 18B similar to the manner in which a violin peg forms an interference fit with the pegbox on the neck of a violin.

By this alternative means of securing the support cone to the boss 16, the support cone can be secured at any rotational position relative to the boss. The plug 18A may be centered within the socket 18B.

Figure 4:
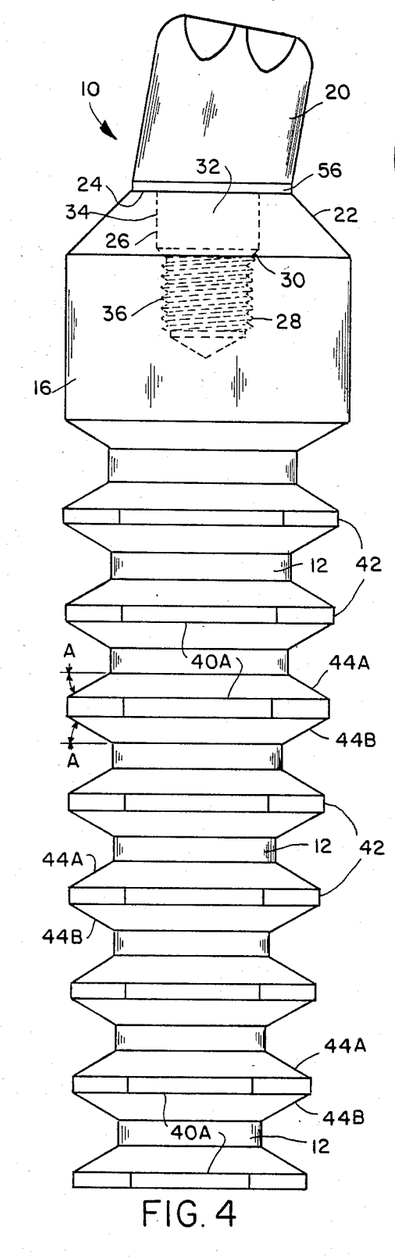
FIG. 4 is a side view of a modified dental implant having fins which are particularly designed to enable the implant to be inserted into sockets in the anterior maxilla.
Figure 5:
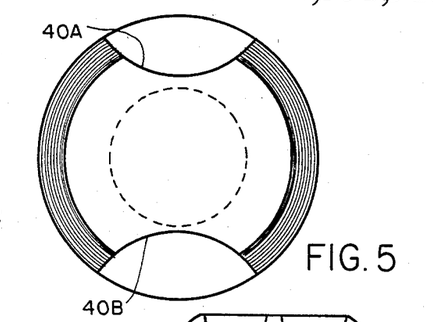
FIG. 5 is a bottom view of FIG. 4.

FIG. 4 illustrates a modified dental implant 10 which is substantially identical to dental implant 10 illustrated in FIG. 1 but includes fins of a different design. Specifically, the fins 42 of this modified dental implant 10 include a conical cross-sectional configuration. Preferably the uper and lower surfaces 44A and 44B are formed at an acute angle with respect to a line extending normally to the post 12 as represented by the angle "A". When utilizing such conically-shaped fins 42 it is noted that the post 12 should be tapered downwardly such that the overall width of the dental implant 10 will progressively decrease downwardly along its entire length thereby conforming to the shape of the socket from which the tooth was extracted. As shown in FIG. 5, a keyway 40A and 40B may be disposed in opposing sides of each of the fins 42 to prevent rotation of the dental implant 10 after installation in the socket of an extracted tooth.

Figure 6:
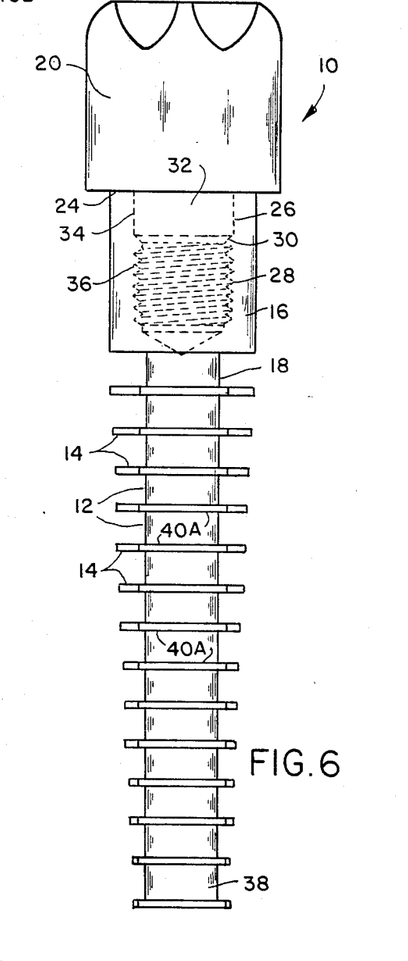
FIG. 6 is a side view of a smaller embodiment of the dental implant shown in FIG. 1.
Figure 7:
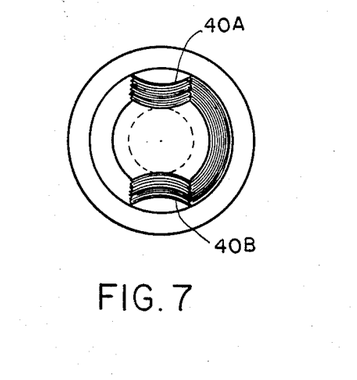
FIG. 7 is a bottom view of FIG. 6.

As noted earlier, the overall width and length of the dental implant 10 should correspond to the size of the socket from which the tooth was extracted. FIG. 6 illustrates a smaller sized dental implant 10 designed to be inserted within smaller sized sockets. This dental implant basically includes the configuration of the dental implant 10 shown in FIG. 1 except for a smaller diameter boss 16 and post 12 and smaller sized fins 14. More particularly, post 12 is reduced in diameter and the fins 14 extending radially therefrom are similarly reduced in their circular cross-sectional area. The keyways 40A and 40B disposed in opposing sides of each of the fins 14 are less than semi-circularly shaped such that the distal end 38 of post 12 is still able to be rigidly connected to the last fin 14 (see FIG. 7). The boss 16 is similarly reduced in diameter, but still includes the counterbore 26 and the threaded hole 28 for receiving the support cone 20. The stud 32 of the support cone 20 threadably engages the threaded hole 28 with shank 34 of the stud 32 engaging into the counterbore 26. The lower surface of the support cone 20 is seated against the upper surface 24 of boss 16.

It should be appreciated that each of the above described dental implants 10 are designed to be inserted within a socket of a recently extracted tooth. It should be understood however, that the dental implant 10 may alternatively be used for insertion into an artificially created socket having a configuration similar to the dental implant 10. After insertion within the socket, the dental implant 10 is left in place for a period of time of approximately two months during which the surrounding bony structure will grow between the fins 14 and 42 thereby rigidly securing the dental implant 10 within the socket. It is noted that a cap screw may be threaded into the threaded hole 28 of boss 16 to prevent matter from entering into and contaminating the counterbore 26 in the threaded hole 28 during this two month period. When the dental implant 10 becomes rigidly secured in the socket, the cap screw is removed and the support cone 20 is then inserted in position into the boss 16. Preferably the threaded hole 28 and the threaded portion 36 of the stud 32 comprise left-handed threads which will not loosen but rather tighten when subjected to any grinding procedures by the dentist. A crown or other prosthesis is then rigidly connected to the support cone 20 by an adhesive or the like.

Figure 8:
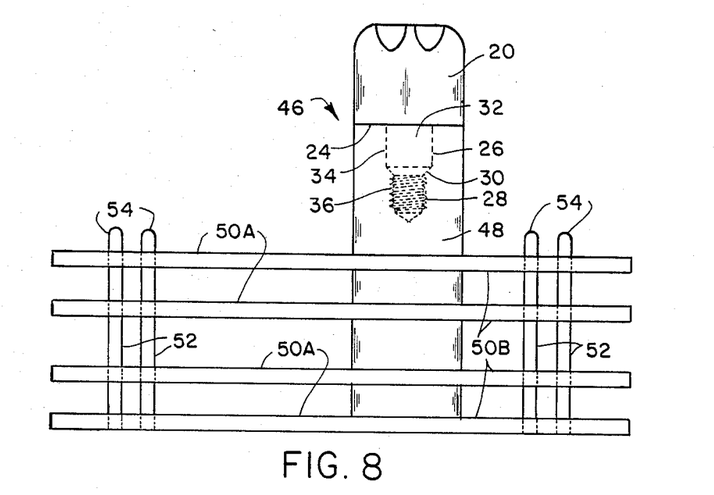
FIG. 8 is a side view of the second embodiment of the dental implant of the invention.
Figure 9:
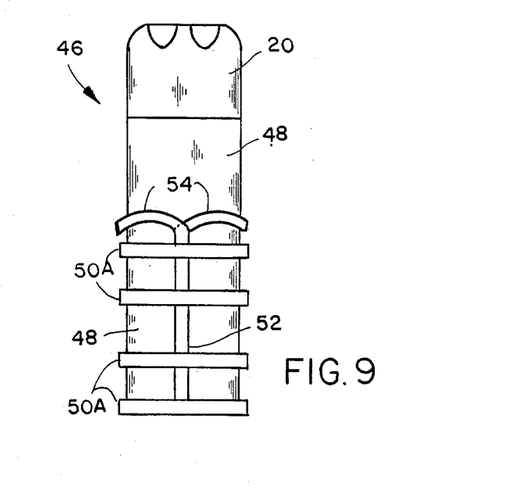
FIG. 9 is a left end view of FIG. 8.
Figure 10:
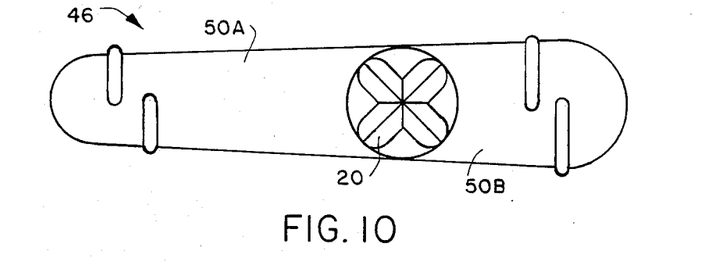

FIGS. 8–10 illustrate the second embodiment of the dental implant 46 of the invention designed to be inserted within an artificially created socket in a jawbone. The dental implant 46 comprises a major post 48 having a plurality of fins 50A and 50B which extend radially outward from diametrically opposite sides of the major post 48 respectively. The fins 50A extending from left of the major post 48 when viewed as shown in FIGS. 8 and 10 include a length greater than the length of those fins 50B extending to the right of the major post 48. As shown in FIG. 10, the fins 50A and 50B when combined, produce a tapered design which tapers from the right fins 50B to the left fins 50A with the ends of each of the fins 50A and 50B being smoothly rounded. As shown in FIGS. 8 and 9, the two lowermost fins constitute a pair and the two uppermost fins constitute a pair such that the distance between the respective fins of each pair is less than the distance between adjacent fins of the lowermost and uppermost pairs respectively. One or more minor posts 52 extend through the stacked left fins 50A. Similarly, one or more minor posts 52 extend through the stacked right fins 50B. Preferably, at least two minor posts 52 are positioned through the respective left or right stacked fins 50A or 50B in close proximity to one another. Further, the upper end 54 of each of the minor posts 52 are preferably curved downwardly as shown in FIG. 9. When using two closely positioned minor posts 52, the upper ends 54 thereof are preferably curved in opposite directions.

The upper end of the major post 48 includes a counterbore 26 and a threaded hole 28 which receives a shank portion 34 and the threaded portion 36 respectively, of the stud 32 extending from the support cone 20.

This second embodiment of the dental implant 46 functions in approximately the same manner as the first embodiment of the dental implant 10. More particularly, the dental implant 46 is inserted into an artificially created receptor site or socket which is formed into the jawbone of the patient by well known dental procedures. Preferably, the receptor site includes a horizontally tapered cross-section corresponding to the configuration of the individual fins 50 and includes a depth sufficient to enable all of the fins 50 to be inserted below the upper surface of the jawbone. The implant 46 is left in position for a substantial amount of time of approximately two months to enable the bone structure to grow between the fins 50. A cap screw may be threaded into the major post 48 to prevent matter from entering into and contaminating the threads of the threaded hole 28. After the implant 46 is rigidly secured within the bone structure of the jawbone, the cap screw is removed and the support cone 20 is then threaded into the threaded hole 28 until the lower surface of the support cone 20 is securely seated against the upper surface 24 of the major post 48. The curved upper ends 54 of the minor posts 52 function to stabilize the gum tissue over the upper surface of the dental implant.

It should be pointed out that this second dental implant 46 of the invention is particularly suitable for installation into artificially created receptor sites in the posterior maxilla to elevate the bony floor of the maxillary sinus thereby creating an equate receptor site in the bone when none naturally exists.

It is noted that in some instances it may be desirable to position the support cone 20 at an angle with respect to the axis of the boss 16. Accordingly, FIG. 4 illustrates a means by which this may be accomplished. Specifically, the tilted relationship of the support cone 20 may be accomplished by angling the stud 32 with respect to the axis of the support cone 20. When the support cone 20 is threaded into boss 16, the support cone 20, when seated against the upper surface 24 of the boss 16 will be tilted at an acute angle. The rotational position of this angle of tilt may be varied by incorporating a washer 56 between the support cone 20 and the boss 16 with the thickness of the washer 56 in proportion to the slope of the threads of the threaded portion 36 determining the rotational position of the angle of tilt. Thus, the rotational position of the tilt with respect to the dental implant 10 is determined by merely selecting a washer 56 having an appropriate thickness with respect to the threads of the threaded portion 36. It is pointed out that this same means for varying the rotational position of tilt of the support cone 20 may also be easily used in conjunction with the first embodiment of the dental implant 10 shown in FIGS. 1 and 6 and the second embodiment of the dental implant 46 shown in FIG. 8.

FIG. 11 illustrates one of the applications of the dental implant shown in FIG. 1A. The upper palate is generally designated 57. The dental implant 10 having oblique fins 14 is disposed in the socket or alveolar of the anterior maxilla or forward portion of the upper jawbone. The fins 14 are disposed at an angle of 30 degrees relative to the central post 12 so as to resist the loading from the lower tooth generally designated 58 as it moves upwards as indicated by the arrow. A crown 17F is shown mounted upon the support cone 20 which is in turn rigidly secured by a threaded stud and corresponding threaded bore defined by boss 16.

In use of the dental implant as described hereinbefore, the dental implant 10 is inserted into the alveolar or socket of an extracted tooth. Unlike the prior art devices, the dental implant of the present invention is not screwed or cemented into the spongy bone walls of the alveolar cavity but rather the spongy bone grows around the fins 14 and firmly anchors the fins within the alveolar cavity. In practice, after two months from implantation, the dental implant is sufficiently anchored to the jawbone to permit the support cone 20 to be threadably secured to the boss 16. During the period of two months while the spongy bone or medulla are growing around the fins, a screw is threaded into the threaded bore of the boss 16 to inhibit the ingress of deleterious matter into the threaded hole 28.

The dental implant shown in FIG. 1 is particularly suited for use in the alveolar cavity of the maxilla or upper jawbone but may equally find usage as a prosthodontic device for the mandible or lower jawbone.

The implant shown in FIGS. 8, 9 and 10 find application in the posterior maxilla, more particularly where the site has been created artificially or where the bony floor of the maxillary sinus is naturally non-existing. In the latter case the implant creates an equate receptor site in the bone.

As the implant device of the present invention is machined from a solid piece of metal, there is no need to assemble the fins to the post as has been the case in some prior art implant devices.

The implant devices of the present invention are primarily intended for use in an artificially created site using conventional site fitting tools which will allow the preparation of the bony sites by using techniques of bone expansion to create sites which are suitable in shape to receive the implants.

The provision of a circumferential sleeve 17 around the sidewalls of the boss 16 creates a smooth non-metallic continuation of the outer surface of the crown 17F. This facilitates stabilization of the gingival mucosa or gum tissue relative to the dental implant.

Implants of the type illustrated in FIGS. 8, 9 and 10 are approximately 3 centimeters in depth, 0.65 centimeters in width and at least 1 centimeter in height. A surgical grade titanium alloy is the preferred material for construction of the main body of the dental implant while the sleeve is of aluminum oxide. The implants shown in FIGS. 1–7 have a diameter from 0.35 centimeters to 0.08 centimeters and a height of 0.2 centimeters to 1.8 centimeters. The washers or shims 56 are of a thickness such that they correspond with quarter, half, and three-quarter turns of the support cone respectively.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A dental implant for suporting a prosthesis, said implant being implantable within a cavity vacated by the extraction of a tooth and suported and anchored therein by ingrowth of bony tissue around and within the implant, said implant comprising:
   an elongated post having a proximal end and a distal end,
   support means for supporting the prosthesis and connected to said post proximal end,
   a multiplicity of fins extending outwardingly from said post between said proximal and distal ends thereof,
   said fins being in spaced and parallel relation to each other along the length of said post, thereby to provide multiple axially extending areas between said fins for ingrowth of bony tissue therebetween as well as therearound to mount said implant firmly in said dental cavity,
   each said fin having a disc-like thin and flat configuration and a width substantially greater than that of said post to provide a substantial surface area for and between said fins for reception of bony tissue ingrowth thereover, thereby to withstand vertical loadings on said implant in use without loosening thereof, and
   at least one said fin having a non-circular configuration in a plane perpendicular to said post, thereby with ingrowth of the bony tissue to preclude rotation of said implant in said dental cavity.

2. The dental implant of claim 1 wherein said fins are individually of successive decreasing transverse width from said post proximal end to said post distal end, thereby to provide said multiplicity of fins with an overall tapered configuration.

3. The dental implant of claim 1, wherein said multiplicity of disc-like fins extend obliquely with respect to said post, thereby to impart the said non-circular configuration to said fins in planes perpendicular to said post.

4. The dental implant of claim 1 wherein said support means includes an upstanding boss connected to said post proximal end, said boss supporting the prosthesis thereupon.

5. The dental implant of claim 4 wherein said support means further includes a support cone carried by said boss and interconnected therewith by means of respective complementary projecting stud and recessed bore means on said support cone and said boss.

6. The dental implant of claim 5 wherein said support cone and said boss are threadably interconnected.

7. The dental implant of claim 6 wherein said stud is angularly positioned with respect to said support cone such that said support cone is angularly tilted with respect to said boss when interconnected therewith.

8. The dental implant of claim 7 further including a washer positioned between said boss and said support cone, the thickness of which thereby predetermines the rotational angular position of said cone.

9. The dental implant of claim 4 further including a circumferential sleeve on and surrounding said boss.

10. The dental implant of claim 9 wherein said boss includes an outwardly extending circumferential ledge upon which said sleeve is seated.

11. The dental implant of claim 10 wherein the upper edge of said sleeve abuts a lower edge of a crown prothesis.

12. The dental implant of claim 9 wherein said sleeve is of ceramic material.

13. The dental implant of claim 9 wherein said sleeve is of aluminum oxide.

14. The dental implant of claim 9 wherein said sleeve is secured to said boss by cement.

15. The dental implant of claim 9 wherein said sleeve is coated onto said boss.

16. The dental implant of claim 9 wherein said sleeve is coated onto said boss by sputtering.

17. The dental implant of claim 1 wherein said fins partake of an elongated tapered planar configuration extending in opposite directions on opposite lateral sides of said post.

18. The dental implant of claim 17 further including a second post extending through said fins at a location laterally spaced from said first-named post to aid in rigidifying said elongated fins.

19. A dental implant, comprising in combination:
   a major post;
   a plurality of first fins extending radially from one side of said major post along the longitudinal length thereof, said fins including an elongated configuration;

a support cone for supporting a prosthesis;

means for connecting said support cone to the proximal end of said major post;

a minor post positioned through said first fins in a position parallel to said major post; and an upper end of said minor post extending from said first fins, said upper end being curved downwardly.

20. A dental implant comprising in combination;

a major post;

a plurality of first fins extending radially from one side of said major post along the longitudinal length thereof, said fins including an elongated configuration;

a support cone threadably secured to the proximal end of said major post by incorporating a stud having a shank portion and a threaded portion to the bottom of said support cone and by incorporating a counter-bore and a threaded hole in the proximal end of said major post for receiving said shank portion and said threaded portion, respectively, of said stud of said support cone;

a first minor post positioned through said first fins in a position parallel to said major post; and a second minor post which is positioned in close proximity to the first minor post and which includes a curved upper end.

21. The dental implant as set forth in claim 20, wherein said upper ends of said first and said second minor posts are curved away from each other.

22. A dental implant, comprising in combination:
a major post;

a plurality of first fins extending radially from one side of said major post along the longitudinal length thereof, said fins including an elongated configuration; and a support cone for supporting a prosthesis, said support cone being threadably secured to the proximal end of said major post by incorporating a stud having a shank portion and a threaded portion to the bottom of said support cone and by incorporating a counterbore and a threaded hole in the proximal end of said major post for receiving said shank portion and said threaded portion, respectively, said stud of said support cone being angularly positioned with respect to said support cone such that said support cone is angularly tilted with respect to the proximal end of said major post when threaded thereto; and a washer positioned between said support cone and said major post for changing the rotational angular position of said support cone.

23. A dental implant, comprising in combination:

an elongated post defining a longitudinal axis therethrough;

a plurality of fins extending along the longitudinal length of said post, each of said fins having a substantially circular configuration disposed within a plane forming an oblique angle with said longitudinal axis;

a boss connected to the proximal end of said post;

a support cone for supporting a prosthesis; and means for connecting said support cone to said boss.

* * * * *

UNITED STATES PATENT AND TRADEMARK OFFICE
CERTIFICATE OF CORRECTION

PATENT NO. : 4,531,915
DATED : July 30, 1985
INVENTOR(S) : O. Hilt Tatum, Jr.

It is certified that error appears in the above-identified patent and that said Letters Patent are hereby corrected as shown below:

In the Specification

Column 3, line 53, after "preparation" insert ".".
    Column 4, line 62, delete "19" and insert therefore --10--.
    Column 6, line 30, delete "uper" and insert therefore --upper--.

In the Claims

Claim 1, line 49, delete "suporting" and insert therefore --supporting--.
    Claim 1, line 51, delete "suported" and insert therefore --supported--.

Signed and Sealed this

Eighth Day of October 1985

[SEAL]

Attest:

DONALD J. QUIGG

Attesting Officer

Commissioner of Patents and Trademarks—Designate